United States Patent
Garbini et al.

(10) Patent No.: US 9,901,711 B2
(45) Date of Patent: Feb. 27, 2018

(54) SHAPE-CONTROLLABLE CATHETERS AND CATHETER SYSTEM

(75) Inventors: Lex J. Garbini, El Granada, CA (US); Mathew Rahimi, Santa Clara, CA (US)

(73) Assignee: SIEMENS MEDICAL SOLUTIONS USA, INC., Malvern, PA (US)

(*) Notice: Subject to any disclaimer, the term of this patent is extended or adjusted under 35 U.S.C. 154(b) by 86 days.

(21) Appl. No.: 13/028,365

(22) Filed: Feb. 16, 2011

(65) Prior Publication Data

US 2012/0209122 A1 Aug. 16, 2012

(51) Int. Cl.
  *A61M 25/01* (2006.01)
  *A61B 8/00* (2006.01)
  *A61M 25/00* (2006.01)

(52) U.S. Cl.
  CPC ......... *A61M 25/0147* (2013.01); *A61B 8/445* (2013.01); *A61M 25/0141* (2013.01); *A61M 25/0082* (2013.01); *A61M 2025/0161* (2013.01)

(58) Field of Classification Search
  CPC .......... A61B 8/445; A61M 2025/0161; A61M 25/0082; A61M 25/0141; A61M 25/0147
  USPC .................. 600/466, 467, 462, 459
  See application file for complete search history.

(56) References Cited

U.S. PATENT DOCUMENTS

| | | | |
|---|---|---|---|
| 4,733,669 A * | 3/1988 | Segal | 600/585 |
| 4,930,521 A | 6/1990 | Metzger et al. | |
| 5,331,947 A * | 7/1994 | Shturman | 600/115 |
| 5,383,852 A * | 1/1995 | Stevens-Wright | 604/95.04 |
| 5,431,673 A * | 7/1995 | Summers et al. | 606/170 |
| 5,441,483 A | 8/1995 | Avitall | |
| 5,846,205 A | 12/1998 | Curley et al. | |
| 5,938,616 A | 8/1999 | Eaton et al. | |
| 6,773,452 B2 | 8/2004 | Shaker | |
| 7,507,205 B2 * | 3/2009 | Borovsky et al. | 600/466 |
| 7,682,319 B2 * | 3/2010 | Martin et al. | 600/585 |
| 7,706,891 B2 | 4/2010 | Hastings et al. | |
| 7,758,623 B2 | 7/2010 | Dzeng et al. | |
| 7,878,977 B2 * | 2/2011 | Mo et al. | 600/459 |
| 8,052,607 B2 | 11/2011 | Byrd | |

(Continued)

FOREIGN PATENT DOCUMENTS

| | | |
|---|---|---|
| JP | 2009-173464 | 8/2009 |
| JP | 2009-273640 | 11/2009 |
| WO | WO 2008/115665 | * 9/2008 |

OTHER PUBLICATIONS

"Yield Curves", Knopman Marks Financial Training, Retrieved Apr. 5, 2016, Available at: http://blog.knopman.com/2014/06/17/yield-curves/.*

(Continued)

*Primary Examiner* — Katherine Fernandez

(57) ABSTRACT

Shape-controllable catheters are provided that are versatile in application and that, in human-imaging applications, minimize or reduce patient discomfort. One such catheter is provided with at least one control wire that extends inside the catheter and a control mechanism for tensioning the control wire to produce in the catheter a humped shape or a cantilevered configuration. Hardness of the catheter may be varied along the length thereof to facilitate desired bending. For example, hardness may be reduced in bend areas. Hardness may be maintained or increased in other areas for performance reasons, for example to maintain planarity of an imaging array.

12 Claims, 4 Drawing Sheets

(56) References Cited

U.S. PATENT DOCUMENTS

| | | |
|---|---|---|
| 8,070,685 B2 | 12/2011 | Harhen et al. |
| 2004/0193021 A1 | 9/2004 | Zdeblick et al. |
| 2005/0187467 A1* | 8/2005 | Kleen .......................... 600/433 |
| 2006/0253115 A1 | 11/2006 | Avitall et al. |
| 2009/0209987 A1* | 8/2009 | Mathews et al. ............. 606/159 |
| 2011/0319910 A1* | 12/2011 | Roelle ................... A61B 34/71 606/130 |

OTHER PUBLICATIONS

Office Action dated Jun. 24, 2014 in counterpart Chinese application No. 201210034898.5, filed Feb. 16, 2012, 15 pages including English translation.

Search Report dated Jun. 16, 2014 in counterpart Chinese application No. 201210034898.5, filed Feb. 16, 2012, 3 pages total.

* cited by examiner

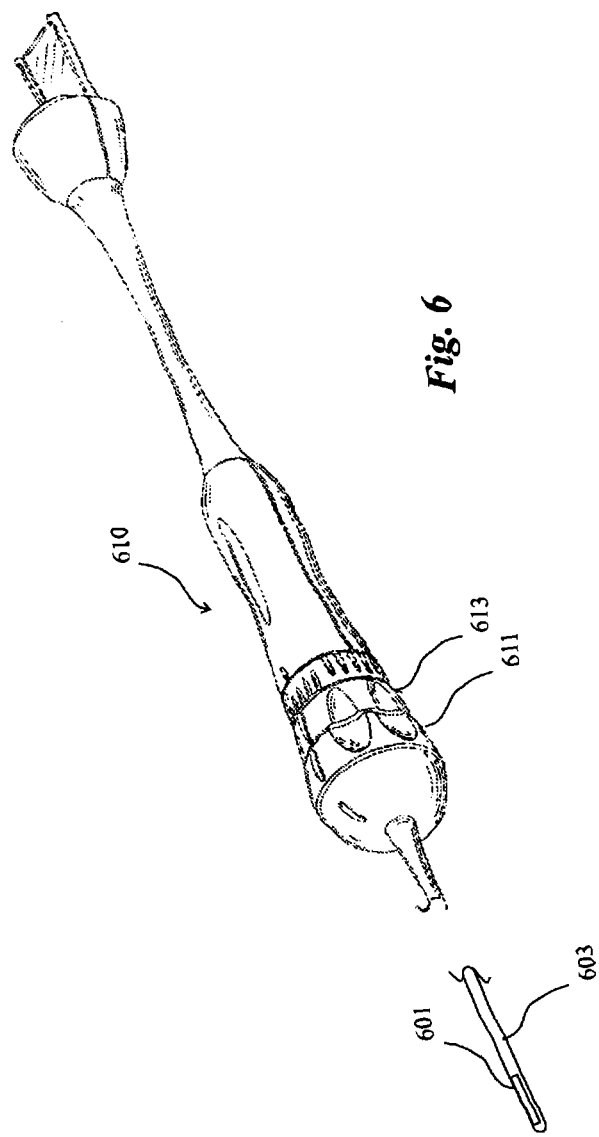

SHAPE-CONTROLLABLE CATHETERS AND CATHETER SYSTEM

BACKGROUND

The present invention relates to catheters and catheter systems, including ultrasound catheter systems.

Various catheter systems, including ultrasound catheter systems, are known. One such catheter system is the Acu-Nav™ catheter system of the present assignee. As shown in FIG. 6, that system uses an ultrasound array 601 mounted at the end of a small-diameter catheter 603 to, in one application, obtain access to the heart through the venous system in order to obtain ultrasound images. Manipulation of the end of the catheter 603 is performed using control wires (not shown) that run through lumens inside the catheter 603. Using four control wires, both anterior/posterior (A/P) and right/left (R/L) control may be achieved. An operator handle 610 is provided with two rotating rings 611 and 613, one for A/P control and one for R/L control. Additional details of the system of FIG. 6 may be found in U.S. Pat. Nos. 5,938,616 and 5,846,205, incorporated herein by reference.

Another known system includes a tubular probe designed for trans-esophageal (TE) use such as trans-esophageal echocardiology (TEE). Cardiac imaging is the most common application. Again, an ultrasound array is mounted at the end of the probe. The probe in this instance, however, is considerably thicker. For an adult version, the probe may be of the approximate thickness of an adult's thumb; for a pediatric version, the probe may be of the approximate thickness of an adult's little finger. Such thicknesses have been required to obtain sufficiently good contact with the esophageal wall to enable effective imaging. The thickness and bulk of these probes produces user discomfort. Furthermore, the versatility of such probe systems is limited. For example, nasal access is not possible with such systems.

SUMMARY

Shape-controllable catheters are provided that are versatile in application and that, in human-imaging applications, minimize or reduce patient discomfort. One such catheter is provided with at least one control wire that extends inside the catheter and a control mechanism for tensioning the control wire to produce in the catheter a humped shape or a cantilevered configuration. Hardness of the catheter may be varied along the length thereof to facilitate desired bending. For example, hardness may be reduced in bend areas. Hardness may be maintained or increased in other areas for performance reasons, for example to maintain planarity of an imaging array. Such catheters may be used instead of and may provide a less expensive alternative to known TE probes.

DRAWING FIGURES

FIG. 6 is a diagram of a known catheter.

DETAILED DESCRIPTION

In the following detailed description, catheter systems are described and shape-controllable catheters are described that can be manipulated to form a curved shape, either a simple curved shape or a compound curved shape. In a relaxed state, insertion of the catheter into a body is readily accomplished. In a non-relaxed state, a contact condition conducive to quality operation may be obtained. In the case of an imaging operation, for example, close and even contact of an imaging array with a body wall may be achieved.

Figure 1A:
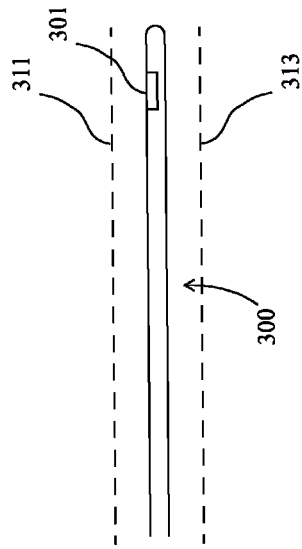
FIG. 1A is a diagram of a shape-controllable catheter in a relaxed state.
Figure 1B:
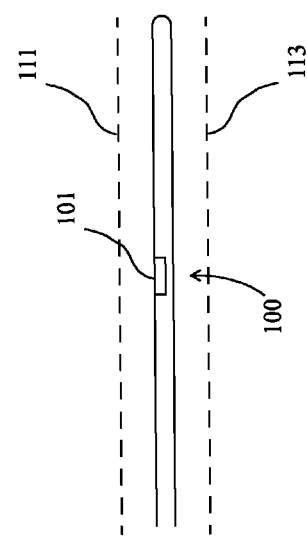
FIG. 1B is a diagram of the catheter of FIG. 1A in a non-relaxed state.

Referring to FIG. 1A and FIG. 1B, perspective views are shown of a portion of one exemplary catheter 100 that can be manipulated to form the shape of a compound curve, for example a reentrant curve. The catheter 100 may be described as a "hump-shaped" catheter in that the catheter 100 may be manipulated (FIG. 1B) to form a hump before the end of the catheter 100. In the case of an ultrasound catheter system, an ultrasound array 101 may be located at the peak point of the hump. Furthermore, in the case of trans-esophageal ultrasound imaging, manipulation of the catheter 100 to form the hump may be used to bring the ultrasound array 101 into intimate contact with the esophageal wall, enabling more effective imaging. Instead of the entire catheter 100 being of a size currently typical of esophageal use, the catheter 100, in a relaxed state (FIG. 1A), may be of a size typical of venous applications. Only in a "hump-shaped" state (FIG. 1B) does the catheter 100 effectively become "esophagus-sized." In this state, a device such as an imaging array 101 is pressed against one wall 111 of the esophagus while nearby portions of the catheter are pressed against an opposite wall of the esophagus 113. A desirable operation condition (for example, imaging array planarity) may be obtained in this manner.

The catheter 100, and other catheters described herein, may be incorporated into a catheter system, for example one that uses the same or similar control mechanism as that illustrated in FIG. 6. They may be used to image any of a wide variety of structures, including living structures (e.g., human and other animal structures) and non-living structures.

Figure 1C:
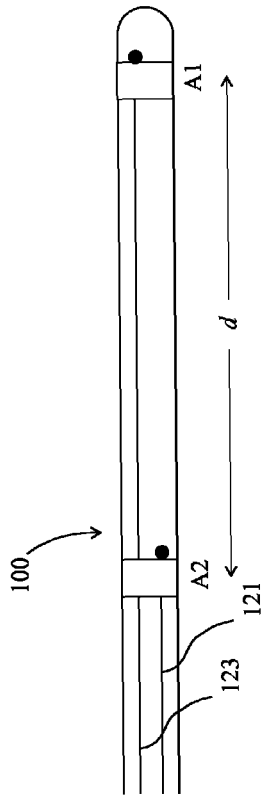
FIG. 1C is a cross-sectional view of a portion of the catheter of FIG. 1A.

Referring to FIG. 1C, a simplified partial longitudinal cross-section is shown of the catheter 100 of FIG. 1A. In one exemplary embodiment, two control wires 121, 123 are used to control the catheter 100 to form a humped shape. Anchor points A1, A2 of the control wires 121, 123 may be such that a first control wire 123 is anchored at a first distance prior to the end of the catheter 100 and a second control wire 121 is anchored at a second distance d prior to the anchor point of the first control wire. In one exemplary embodiment, the first distance may be about a few centimeters, and the second distance d may be about 6-9 centimeters (e.g., about three inches). The two control wires 121, 123 may be provided in addition to control wires providing A/P and L/R control. Alternatively, two of the existing control wires in an existing catheter system (for example, the L/R control wires) may be re-purposed to provide control of the hump-shaped feature.

Note that the foregoing arrangement is exemplary only. The catheter system may use other controls or additional controls. For example, an angular control may be provided as described, for example, in U.S. Patent Application 2008/0146941, incorporated herein by reference.

In other embodiments, stiffness of the catheter may be varied strategically in order to promote a desired configuration of the catheter in a flexed state. For example, the stiffness of the catheter may be reduced on one side or on both sides of the operative device, such as an ultrasound array. In the area of the ultrasound array itself, the catheter may be kept relatively stiff, or even made more stiff, in order to maintain planarity of the array. In one exemplary embodiment, such variation in stiffness may be achieved by using polymer materials of different hardnesses, one such family of suitable polymer materials being Pebax™ polymer materials. Using the Shore D hardness scale, hardness in the area of the ultrasound array may be around 40d, while hardness in areas on both sides of the ultrasound array may be reduced to around 25d. A resulting configuration of a catheter 200 in a flexed state is shown in FIG. 2, the catheter 200 having areas of reduced stiffness on either side of the ultrasound array 201, such as those areas marked by "X" in FIG. 2.

Figure 3A:
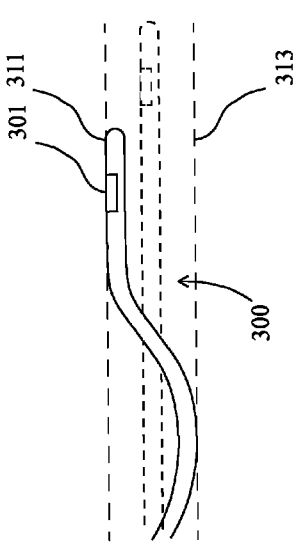
FIG. 3A is a diagram of another shape-controllable catheter in a relaxed state.
Figure 3B:
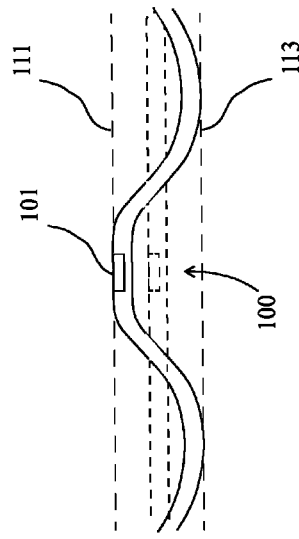
FIG. 3B is a diagram of the catheter of FIG. 3A in a non-relaxed state.

In still further embodiments, the catheter may be configured so as to produce a single bend using a single control wire, as illustrated for example in FIGS. 3A and 3B. Such a catheter 300 may be referred to as "cantilevered," since in a non-relaxed state a device 301 (such as an imaging array) is borne on a length of the catheter that is supported at one end and that, relative to the remainder of the catheter 300, projects away and forward.

Figure 4:
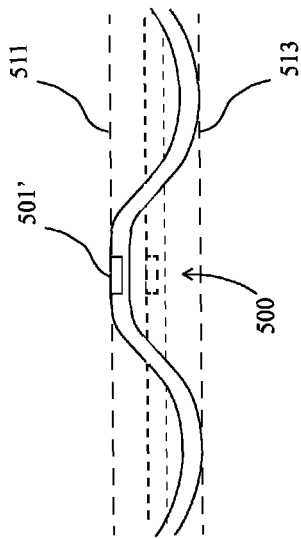
FIG. 4 is a diagram of another catheter in a non-relaxed state.

Another example of a cantilevered catheter 400 is shown in FIG. 4, the cantilevered catheter 400 being provided with an operative device such as an ultrasound array 401. In the area of the ultrasound array 401 itself, the catheter 400 may be kept relatively stiff, or even made more stiff, in order to maintain planarity of the array 401. In one exemplary embodiment, stiffness in the area of the ultrasound array 401 may be around 40d, while stiffness in other areas such as the marked by "X" on the near side of the ultrasound array 401 may be reduced to around 25d.

Figure 1D:
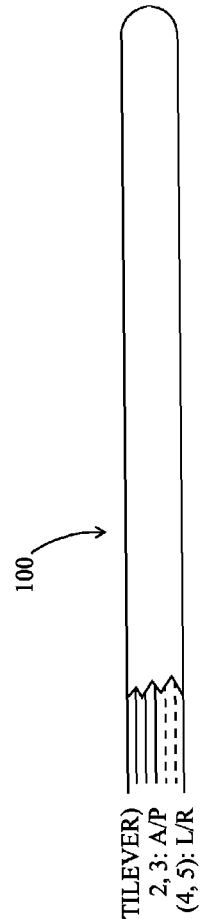
FIG. 1D is a partial cutaway view of a catheter like those of FIGS. 1 and 3.
Figure 1E:
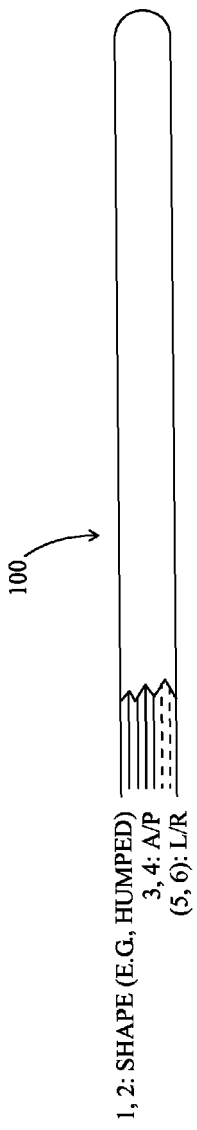
FIG. 1E is partial cutaway view of a catheter like those of FIGS. 2 and 4.
Figure 2:
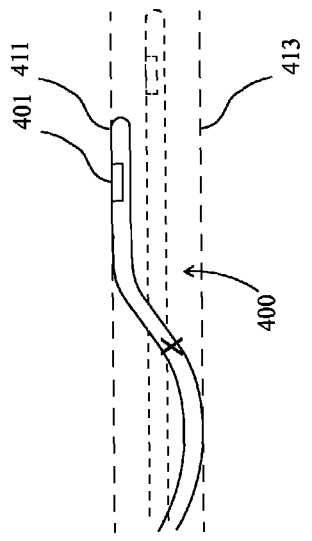
FIG. 2 is a diagram of another catheter in a non-relaxed state.

Referring to FIG. 1D and FIG. 1E, partial cutaway views are shown of catheters like those of FIGS. 1 and 3 and those of FIGS. 2 and 4, respectively, showing in greater detail possible arrangements of control wires. As seen in FIG. 1D, in the case of a catheter configured to assume a cantilevered configuration, a first control wire may be used to control shape. Second and third control wires may be used for articulation in one plane, for example A/P articulation. Optionally, fourth and fifth control wires may be used for articulation in another plane, for example L/R articulation. As seen in FIG. 1E, in the case of a catheter configured to assume a humped shape, first and second control wires may be used to control shape. Third and fourth control wires may be used for articulation in one plane, for example A/P articulation. Optionally, fifth and sixth control wires may be used for articulation in another plane, for example L/R articulation.

In the case of trans-esophageal use of a hump-shaped ultrasound catheter, typically a series of images will be acquired. For each image acquisition, the catheter may be manipulated to cause it to go from a relaxed state to a hump-shaped state. Between image acquisitions, the catheter may be allowed to resume a relaxed state during which the position of the catheter may be adjusted, for example.

Similarly, in the case of trans-esophageal use of a cantilevered ultrasound catheter, for each image acquisition, the catheter may be manipulated to cause it to go from a relaxed state to a hump-shaped state. Between image acquisitions, the catheter may be allowed to resume a relaxed state during which the position of the catheter may be adjusted, for example.

Figure 5:
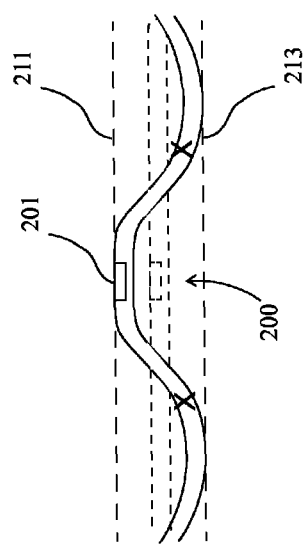
FIG. 5 is a diagram of another catheter in a non-relaxed state.

Referring to FIG. 5, in another embodiment, a catheter 500 like that of any of the preceding figures, such as that of FIG. 1A, may be provided with a device or combination of devices 501' that includes a pressure sensor or otherwise incorporates pressure sensing capabilities. One of the advantages of the present catheters and catheter systems is the ability to achieve greater pressure (and greater uniformity of pressure) of an imaging device or other device against a vessel wall. Using the catheter 500 and the device(s) 501', a pressure reading may be obtained during control of the catheter 500. This pressure information may be displayed and/or recorded, either periodically, continuously in real time, or upon the occurrence of certain events.

The foregoing pressure information may be used in various ways. For example, if the pressure information is displayed continuously to an operator, the operator may initiate an imaging operation or other operation only when pressure conditions are such as to ensure satisfactory results. In other embodiments, pressure information may be used for elastography or the like. Elastography uses pressure applied to tissue to obtain information about the tissue. For example, if tissue is abnormally stiff, such stiffness may be indicative of a tissue abnormality. In other instances, if tissue is abnormally soft, such softness may be indicative of a tissue abnormality. Using the catheter 500 and the device(s) 501', various techniques may be used to sense tissue stiffness. To take one example, from the onset of measurable pressure against the vessel wall, the rate at which pressure increases may be taken as an indication of tissue stiffness. If the pressure increases abnormally quickly, such rapid increase may be attributed to abnormally stiff tissue. If the pressure increases abnormally slowly, such slow increase may be attributed to abnormally soft tissue.

Although the shape-controllable catheters described herein are especially suitable for imaging applications using imaging devices, any of various kinds of devices may be mounted in or on the catheter, including both imaging and non-imaging devices, electronic devices, mechanical devices, pharmacological devices, etc.

The described shape-controllable catheters are versatile in application. Because of their relatively small diameter, the catheters are suitable for nasal insertion, for example. In the case of an imaging operation, close and even contact of an imaging array with a body wall may be achieved. Moreover, in human-imaging applications, because of the relatively small diameter of the catheters, patient discomfort is minimized or reduced.

It will be appreciated by those of ordinary skill in the art that the present invention can be embodied in other specific forms without departing from the spirit or essential character thereof. The foregoing description is therefore considered in all respects to be illustrative and not restrictive. The scope of the invention is indicated by the appended claims, not the foregoing description, and all changes that come within the meaning and range of equivalents thereof are intended to be embraced therein.

What is claimed is:

1. An apparatus comprising:
   a catheter having an exterior comprising materials manufactured to have different hardnesses such that a hardness of the catheter varies along a length of the catheter;
   at least one control wire that extends inside the catheter and is anchored inside the catheter at a point along the length of the catheter; and
   a control mechanism for tensioning the at least one control wire to produce in the catheter a plurality of curves resulting in a humped shape in a portion of the catheter, the humped shape comprising a hump formed from the plurality of curves,
   wherein the hardness varies along the length of the catheter so that one of a plurality of regions of relatively lesser hardness are provided on both sides of at least one region of relatively greater hardness corresponding to the hump when the catheter is in the humped shape.

2. The apparatus of claim 1, comprising an ultrasound transducer array mounted in or on the catheter.

3. The apparatus of claim 2, wherein the ultrasound transducer array is mounted at a location removed from the distal end of the catheter by at least two centimeters.

4. The apparatus of claim 3, wherein the ultrasound transducer array is mounted at a location removed from the distal end of the catheter, the location including an apex of said humped shape.

5. The apparatus of claim 4, wherein the apex with the ultrasound transducer array comprises a straight portion of the hump with at least two of the plurality of curves distal to the straight portion and at least two of the plurality of curves proximal to the straight portion.

6. The apparatus of claim 2, wherein the ultrasound transducer array is mounted in the at least one region of relatively greater hardness.

7. The apparatus of claim 1, wherein the at least one control wire comprises first and second control wires that extend inside the catheter and are anchored inside the catheter at respective anchor points at different lengths along the length of the catheter, wherein the control mechanism is configured for tensioning the control wires to produce in the catheter said humped shape.

8. The apparatus of claim 7, wherein the at least one control wire further comprises third and fourth control wires that extend inside the catheter and are anchored inside the catheter at respective anchor points;
   wherein the third and fourth control wires are configured to provide anterior/posterior control or left/right control of a tip of the catheter.

9. The apparatus of claim 8, wherein the at least one control wire further comprises fifth and sixth control wires that extend inside the catheter and are anchored inside the catheter at respective anchor points;
   wherein the fifth and sixth control wires are configured to provide another of anterior/posterior or left/right control of the tip of the catheter.

10. An apparatus comprising:
    a catheter including an exterior;
    at least one control wire that extends inside the catheter and is anchored inside the catheter at a point along the catheter; and
    a control mechanism for tensioning the at least one control wire to produce a cantilevered configuration in a length of the catheter extending from a distal end of the catheter, wherein the cantilevered configuration results in the length of the catheter extending from the distal end positioned straight and parallel to an axis defined by the catheter having an un-tensioned control wire;
    wherein the exterior of the catheter comprises materials manufactured to have different hardnesses such that hardness varies along the length of the catheter, comprising a region of greater hardness in the length of the catheter extending from the distal end of the catheter and at least one region of lesser hardness corresponding to a proximal bend in the catheter.

11. The apparatus of claim 10, comprising an ultrasound array located in or on the catheter within the length of the catheter extending from the distal end of the catheter.

12. The apparatus of claim 10, wherein the at least one control wire comprises a single control wire to produce the bend in the catheter, wherein the length of the catheter extending from the distal end of the catheter is supported by and projects away from the bend in the catheter.

* * * * *